(12) United States Patent
Chuang et al.

(10) Patent No.: US 9,856,291 B2
(45) Date of Patent: Jan. 2, 2018

(54) CANCER STEM CELL TARGETING PEPTIDE AND USE THEREOF

(71) Applicant: AGRICULTURAL TECHNOLOGY RESEARCH INSTITUTE, Hsinchu (TW)

(72) Inventors: Chin-Kai Chuang, Taipei (TW); Yu-Hsyu Su, Taipei (TW); Tai-Yun Lin, Taipei (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/373,254

(22) Filed: Dec. 8, 2016

(65) Prior Publication Data
US 2017/0158737 A1 Jun. 8, 2017

(30) Foreign Application Priority Data

Dec. 8, 2015 (TW) .............................. 104141210 A

(51) Int. Cl.
| | | |
|---|---|---|
| A61K 38/00 | (2006.01) | |
| A61K 38/04 | (2006.01) | |
| A61K 38/06 | (2006.01) | |
| C07K 7/00 | (2006.01) | |
| C07K 7/06 | (2006.01) | |
| C12N 15/10 | (2006.01) | |
| G01N 33/574 | (2006.01) | |
| G01N 33/50 | (2006.01) | |

(52) U.S. Cl.
CPC ............ *C07K 7/06* (2013.01); *C12N 15/1037* (2013.01); *G01N 33/5073* (2013.01); *G01N 33/574* (2013.01); *G01N 33/57484* (2013.01); *A61K 38/00* (2013.01)

(58) Field of Classification Search
CPC ........ A61K 38/00; A61K 38/04; A61K 38/06; C07K 7/00; C07K 7/06
USPC ............................... 514/19.3, 21.7; 530/329
See application file for complete search history.

(56) References Cited

U.S. PATENT DOCUMENTS

| | | | | |
|---|---|---|---|---|
| 6,465,229 B2* | 10/2002 | Cahoon | ................ | C12N 9/1007 435/193 |
| 6,747,137 B1* | 6/2004 | Weinstock | ........... | C12Q 1/6895 435/6.13 |
| 7,214,786 B2* | 5/2007 | Kovalic | ............... | C07K 14/415 530/324 |
| 7,314,974 B2* | 1/2008 | Cao | ...................... | C07K 14/195 800/288 |
| 7,381,817 B2* | 6/2008 | Paranhos-Baccala | ..................... | C07K 14/005 424/207.1 |
| 7,745,391 B2* | 6/2010 | Mintz | ..................... | G06F 19/24 514/19.3 |
| 8,119,385 B2* | 2/2012 | Mathur | .................... | C12N 9/00 435/212 |
| 8,541,208 B1* | 9/2013 | Plesch | .................. | C07K 14/245 435/106 |
| 9,029,636 B2* | 5/2015 | Wu | ....................... | C07K 14/415 435/419 |
| 9,073,990 B2* | 7/2015 | Paas | .................. | A61K 47/48338 |
| 9,238,822 B2* | 1/2016 | Baum | ..................... | A01N 63/02 |
| 9,441,255 B2* | 9/2016 | Tian | ........................ | C07K 14/37 |

OTHER PUBLICATIONS

A0A0D8HK93 from UniProt, pp. 1-4. Integrated into UniProtKB/TrEMBL on May 27, 2015.*
A0A090T3A9 from UniProt, pp. 1-3. Integrated into UniProtKB/TrEMBL on Nov. 26, 2014.*

\* cited by examiner

*Primary Examiner* — Julie Ha
(74) *Attorney, Agent, or Firm* — Birch, Stewart, Kolasch & Birch, LLP

(57) ABSTRACT

A synthetic peptide that targets cancer stem cells is provided. The peptide consists of the amino acid sequence of anyone of SEQ ID NO: 1 to SEQ ID NO: 15. Also provided is a composition comprising said synthetic peptide with a therapeutic agent fused thereto, and a pharmaceutically acceptable carrier or diluent. Further provided is a method of screening a peptide specifically targeting to a cancer stem cell. The method comprises the steps of establishing an oligopeptide library by using a phage expression system, contacting the library with a culture of bulk tumor cells of a cancer cell line, contacting the phages which do not bind to the bulk tumor cells with a culture of cancer stem cells of said cancer cell line, and screening a peptide specifically targeting to a cancer stem cell from the phages which bind to the cancer stem cells.

7 Claims, 6 Drawing Sheets
(2 of 6 Drawing Sheet(s) Filed in Color)

US 9,856,291 B2

CANCER STEM CELL TARGETING PEPTIDE AND USE THEREOF

FIELD OF THE INVENTION

The present invention pertains to a synthetic peptide that targets cancer stem cells. The present invention also relates to a pharmaceutical composition comprising such synthetic peptide with a therapeutic agent. In another aspect, the invention pertains to a method of screening a peptide specifically targeting to a cancer stem cell.

BACKGROUND OF THE INVENTION

Since the first discovery of cancer stem cell (CSC) of acute myeloid leukemia (AML) in 1994, the identifications of CSCs were further demonstrated in breast cancer, brain cancer, liver cancer, colon cancer, lung cancer and pancreatic cancer. Besides the self-renewal activity of normal stem cell, CSCs are resistant to chemotherapy, radiotherapy, hypoxia, and immune-surveillance. In addition, CSCs are thought to be the major reason of cancer relapse.

There remains a need for an agent which specifically targets to cancer stem cells, for therapeutic, imaging and other purposes.

BRIEF SUMMARY OF THE INVENTION

In one aspect, the present invention provides a synthetic peptide that targets cancer stem cells, which consists of the amino acid sequence of anyone of SEQ ID NO: 1 to SEQ ID NO: 15.

In the embodiments of the present invention, the synthetic peptide is for use in diagnosing a cancer. According to some other embodiments of the present invention, the peptide is for use in targeting a therapeutic agent to a cancer stem cell.

According to the present invention, the synthetic peptide may be fused to a detectable moiety. In certain embodiments of the present invention, the detectable moiety is a radiolabel, a fluorophore, or a magnetic imaging contrast agent.

According to the present invention, the synthetic peptide may be fused to a therapeutic agent. In certain preferred embodiments of the present invention, the therapeutic agent is an anti-tumor agent. The anti-tumor agent includes but is not limited to a chemotherapeutic agent, a radiotherapeutic agent or an immunotherapeutic agent.

In another aspect, the present invention provides a composition comprising a synthetic peptide according to the present invention, and a pharmaceutically acceptable carrier or diluent. Preferably, the synthetic peptide is fused to a therapeutic agent.

In one further aspect, the present invention provides a method of screening a peptide specifically targeting to a cancer stem cell, comprising establishing an oligopeptide library by using a phage expression system, contacting phages in the library with a culture of bulk tumor cells of a cancer cell line, contacting the phages which do not bind to the bulk tumor cells with a culture of cancer stem cells or cancer stem cell like cells of said cancer cell line, and screening a peptide specifically targeting to a cancer stem cell from the phages which bind to the cancer stem cells or cancer stem cell like cells.

It is to be understood that both the foregoing general description and the following detailed description are exemplary and explanatory only and are not restrictive of the invention.

BRIEF DESCRIPTION OF THE SEVERAL VIEWS OF THE DRAWINGS

The patent or application file contains at least one drawing executed in color. Copies of this patent or patent application publication with color drawing(s) will be provided by the office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred.

In the drawings:

Figure 1A:
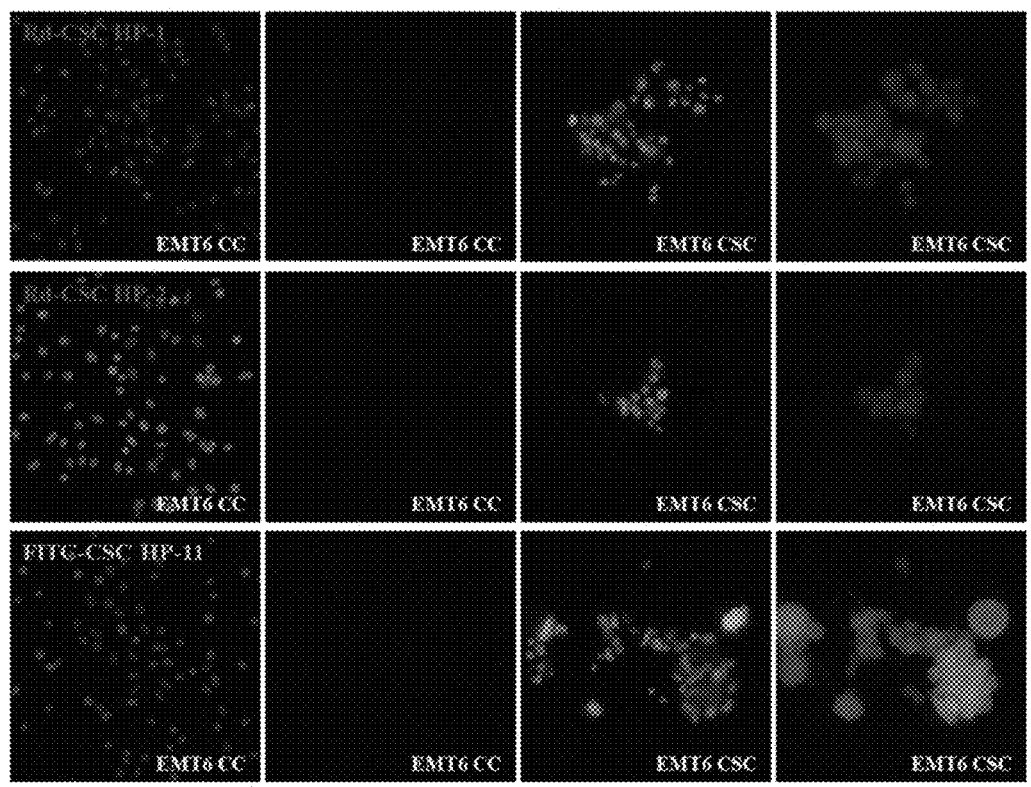

FIG. 1A shows that selective binding of cancer stem cell (CSC) homing peptides (HPs) to CSCs. Rhodamine B labeled CSC HP1 (Rd-CSC HP-1) and CSC HP2 (Rd-CSC HP-2) as well as FITC labeled CSC HP11 (FITC-CSC HP-11) were directly used to stain EMT6 CSCs and CCs. Cells were counter-stained with DAPI. Fluorescence images were taken at the same exposure conditions.

Figure 1B:
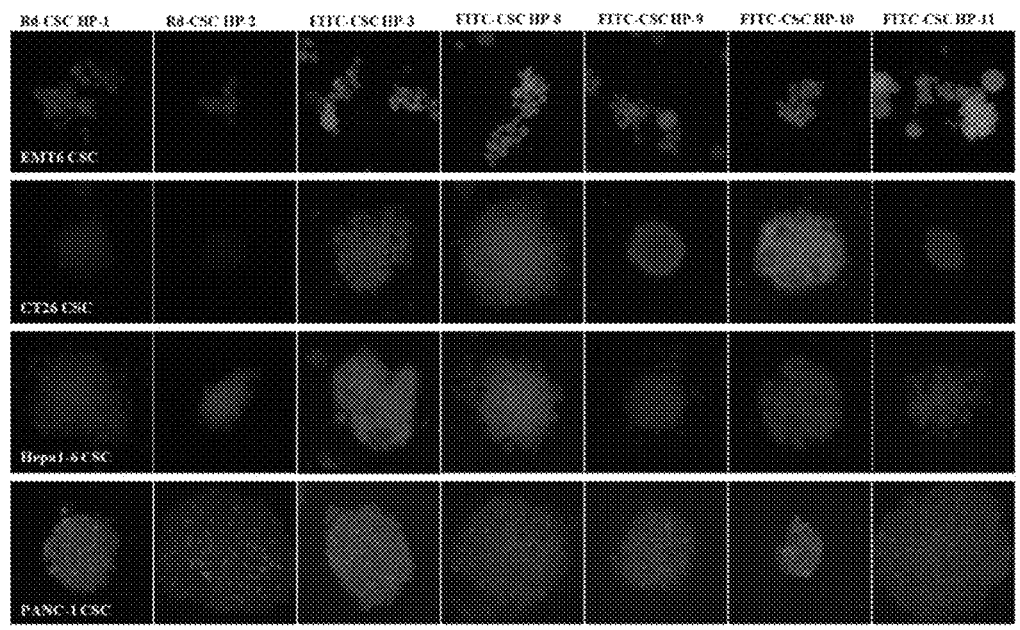

FIG. 1B shows that selective binding of CSC HPs to CSCs. The CSCs of EMT-6, CT26, Hepal-6 and PANC-1 were separately stained with Rd-CSC HP-1, Rd-CSC HP-2, FITC-CSC HP-3, FITC-CSC HP-8, FITC-CSC HP-9, FITC-CSC HP-10 or FITC-CSC HP-11. Fluorescence images were taken at the same exposure conditions.

Figure 2:
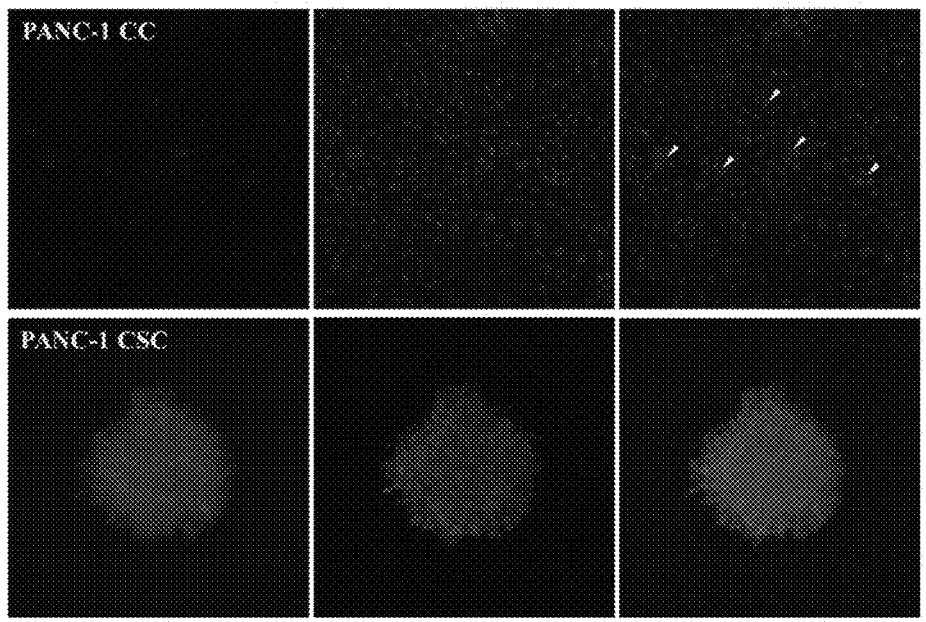

FIG. 2 shows the binding of CSC HP-hP1-DsRed to PANC-1 CCs and CSCs. CSC HP-hP1-DsRed recombinant protein, final concentration of 25 µg/mL, was used to stain PANC-1 CCs and CSCs. The arrowheads indicated the weak signals observed in the PANC-1 CC case.

Figure 3A:
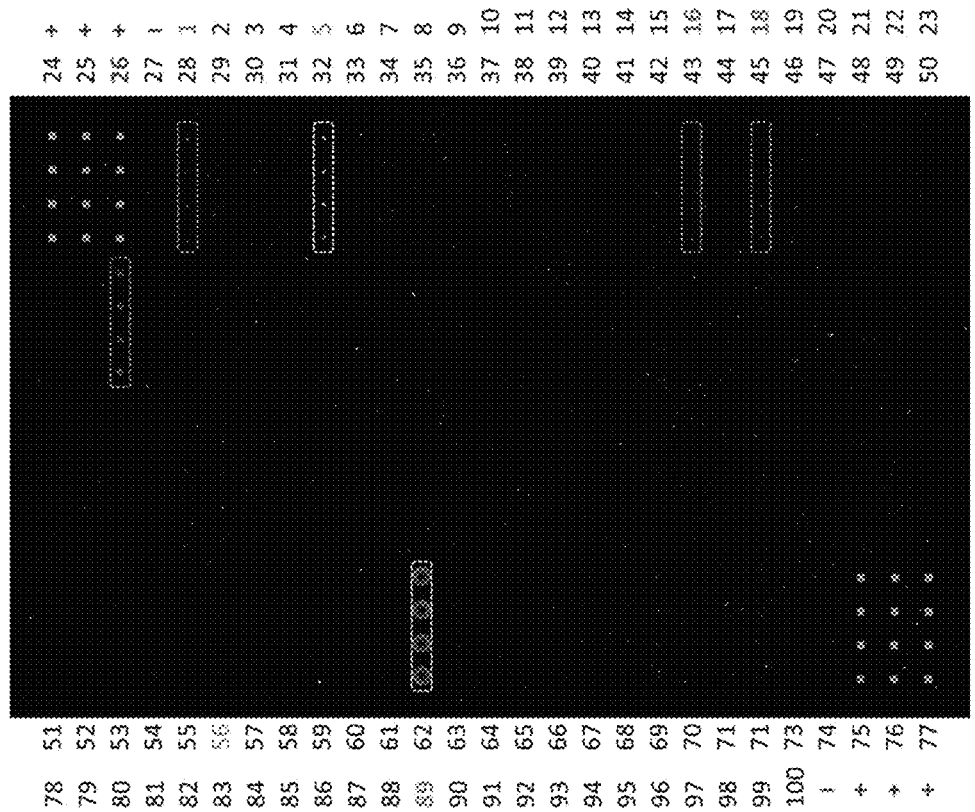
Figure 3B:
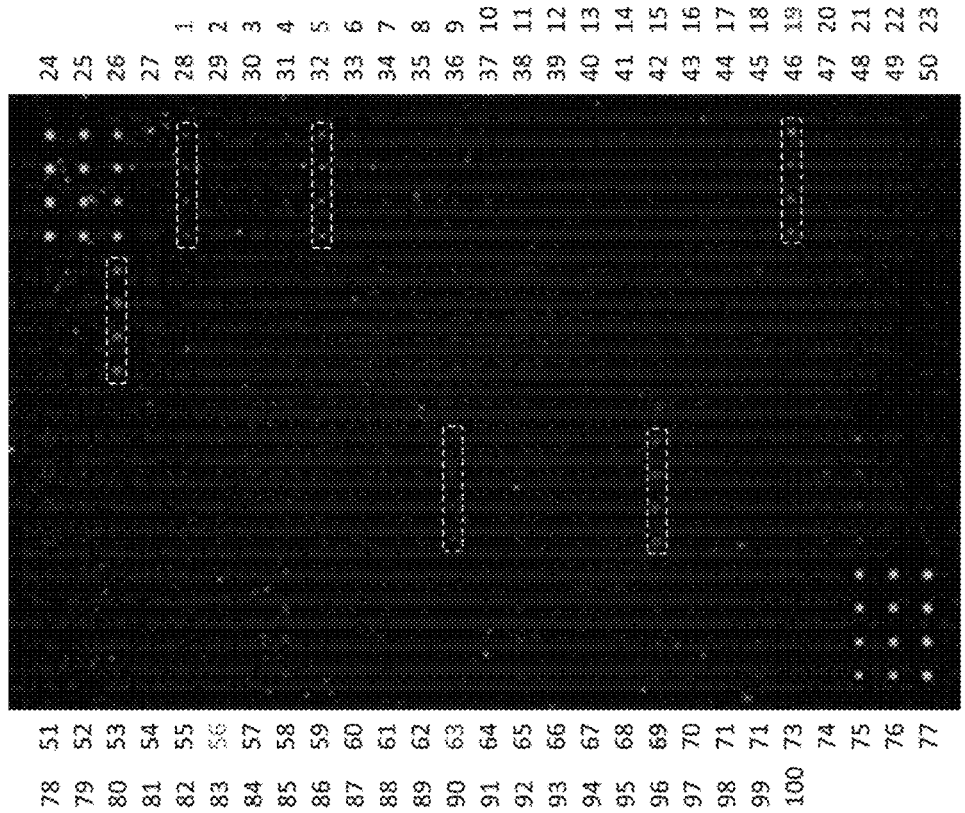
Figure 3C:
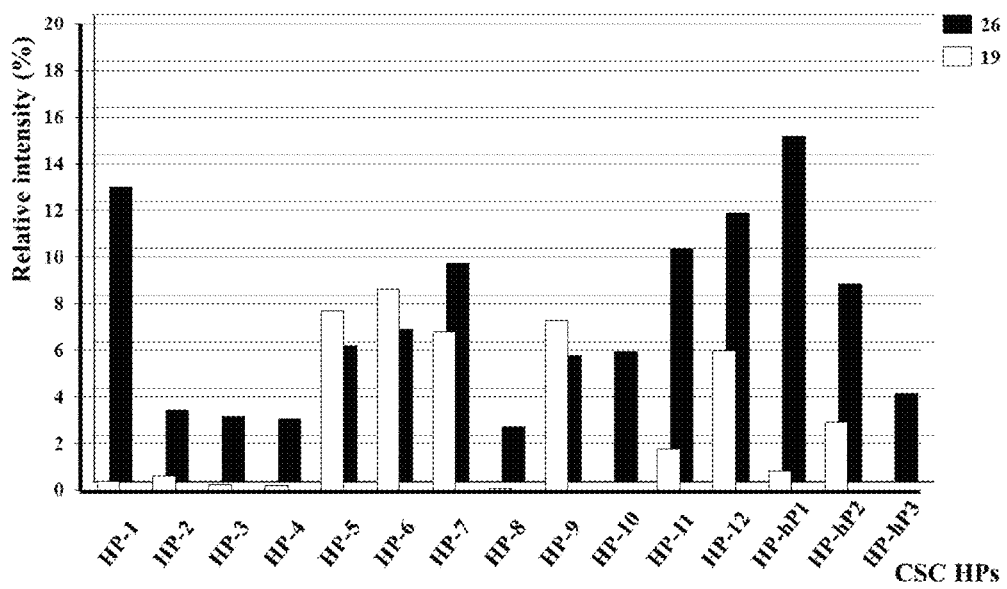
Figure 3D:
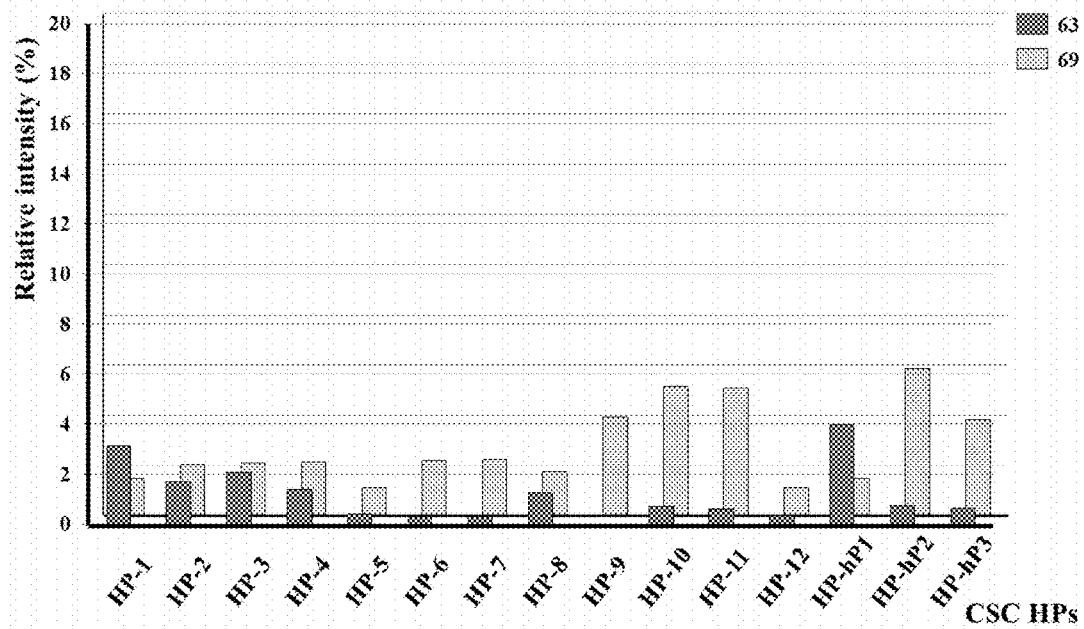
Figure 3E:
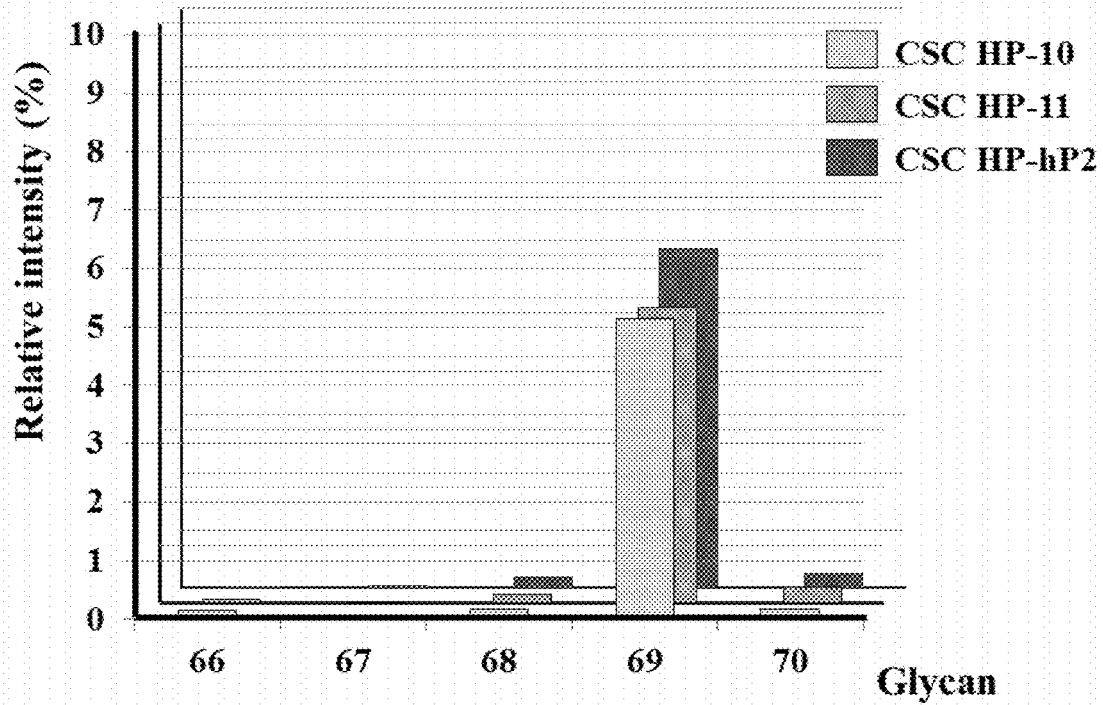
Figure 3F:
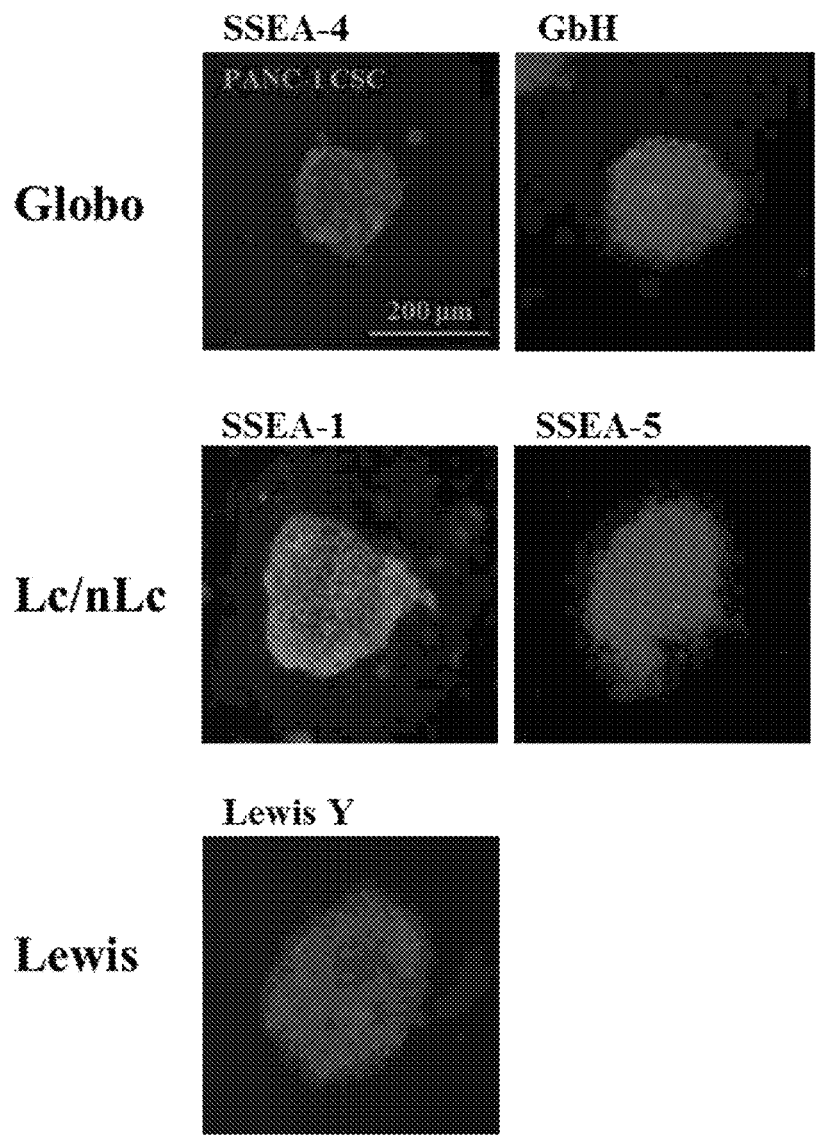

FIGS. 3A-3F show the targets of CSC HPs analyzed by glycan microarray and immunofluorescence (IF). FIG. 3A shows the results of glycan microarray analysis of CSC HP-hP1-labeled with biotin. FIG. 3B shows the results of glycan microarray analysis of CSC HP-9 labeled with biotin. FIG. 3C shows the relative intensities of a Globo series glycan (glycan 26) versus a Lacto/Neolacto series glycan (glycan 19) signals, which were normalized with the positive control signal 3 of the same microarray collected from the 15 CSC HPs. FIG. 3D shows the relative intensities of glycan 63 and glycan 69 signals from the 15 CSC HPs. FIG. 3E shows the relative intensities of glycan 66 (Gal-β-1,3-GalNAc-β-), glycan 67 (Gal-β-1,3-(Neu5Ac-α-2,6)-GalNAc-β-), glycan 68 (Neu5Ac-α-2,6-Gal-β-1,3-GalNAc-β-), glycan 69 (Neu5Ac-α-2,6-Gal-β-1,3-(Neu5Ac-α-2,6)-GalNAc-β-), and glycan 70 (Neu5Ac-α-2,3-Gal-β-1,3-(Neu5Ac-α-2,6)-GalNAc-β-) signals collected from CSC HP-10, CSC HP-11, and CSC HP-hP2 chips. FIG. 3F is the IF images of stem-cell-specific glycan markers on PANC-1 CSCs performed with monoclonal antibodies against Globo series (SSEA-4 and GbH), Lacto/Neolacto (Lc/nLc) series (SSEA-1 and SSEA-5), and Lewis Y.

Figure 4A:
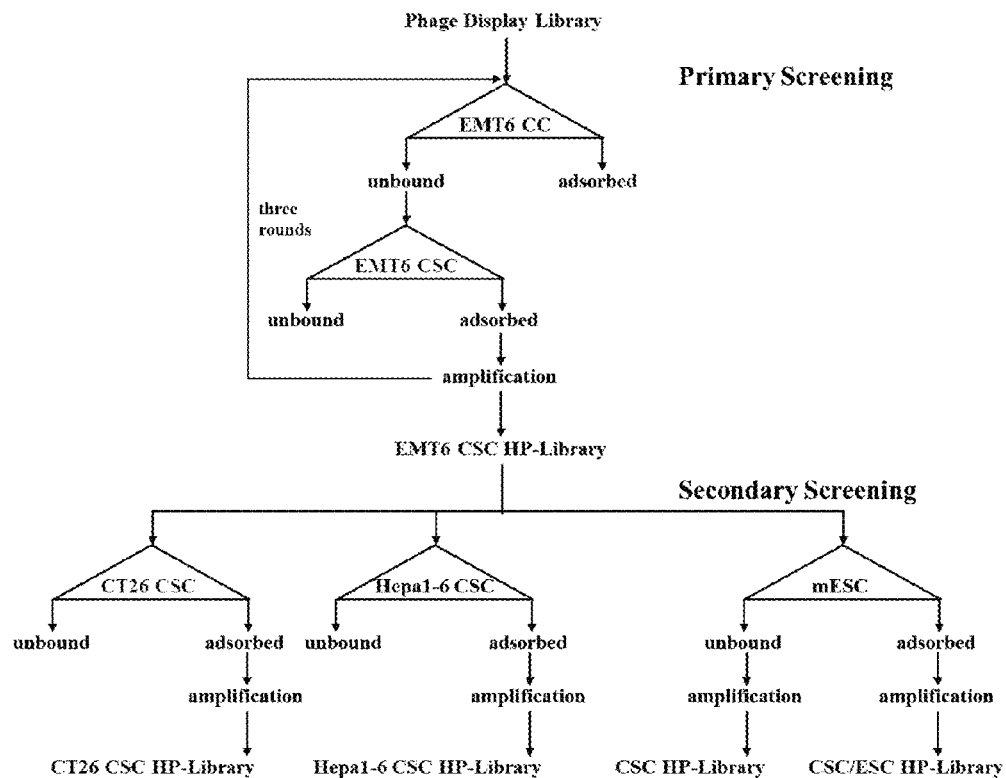

FIG. 4A is a flowchart showing the primary screening from the original M13 PhD7 library to prepare the EMT6 CSC HP-Library, and the secondary screening to produce the CT26 CSC HP-Library, the Hepal-6 CSC HP-Library, the CSC/ESC HP-Library, and the CSC HP-Library.

Figure 4B:
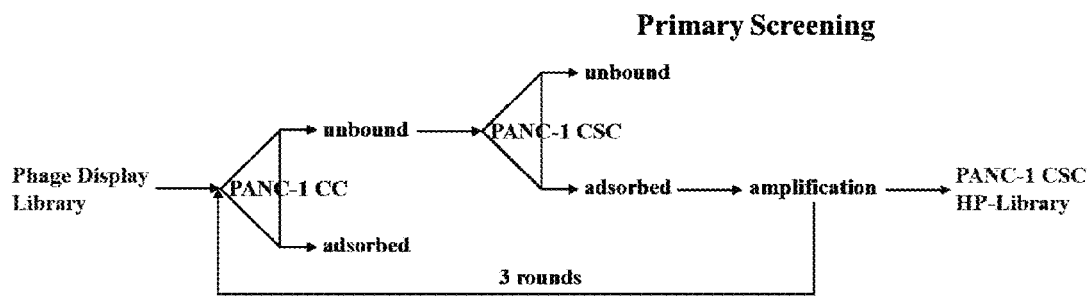

FIG. 4B is a flowchart illustrating establishment of the PANC-1 CSC HP-library.

DETAILED DESCRIPTION OF THE INVENTION

Unless defined otherwise, all technical and scientific terms used herein have the same meaning as commonly understood by a person skilled in the art to which this invention belongs.

In one aspect, the present invention provides a synthetic peptide that targets cancer stem cells, which consists of the amino acid sequence of anyone of SEQ ID NO: 1 to SEQ ID NO: 15. The synthetic peptide of the present invention selectively or specifically homes to cancer stem cells, and thus is useful in the form of a conjugate for selectively targeting a systemically administered therapeutic agent to the cancer stem cells. Such selective targeting of a therapeutic agent increases the effective amount of an agent delivered to the cancer stem cells while reducing the likelihood that the agent will have an adverse effect on other cells or other parts of the body.

The term "cancer stem cells (CSCs)" as used herein refers to cancer stem cells of mammals, for example, mice of humans.

The synthetic peptide of the present invention homes to, targets to, or specifically binds to CSCs, but does not or very weakly binds to (normal) cancer cells (CCs). The cancer stem cells are of a cancer includes but is not limited to a breast cancer, a liver cancer, a pancreatic cancer, and a colon cancer.

According to one embodiment of the present invention, the synthetic peptide consists of the amino acid sequence SQPTWMF (SEQ ID NO: 1) (also called as CSC HP-1). In one embodiment, CSC HP-1 homes to, targets to, or specifically binds to CSCs of a breast cancer. In another embodiment, CSC HP-1 homes to, targets to, or specifically binds to CSCs of a colon cancer.

According to one embodiment of the present invention, the synthetic peptide consists of the amino acid sequence GMMSSPP (SEQ ID NO: 2) (also called as CSC HP-2). In one embodiment, CSC HP-2 homes to, targets to, or specifically binds to CSCs of a breast cancer. In another embodiment, CSC HP-2 homes to, targets to, or specifically binds to CSCs of a colon cancer.

According to one embodiment of the present invention, the synthetic peptide consists of the amino acid sequence FSGGGNH (SEQ ID NO: 3) (also called as CSC HP-3). In one embodiment, CSC HP-3 homes to, targets to, or specifically binds to CSCs of a breast cancer. In another embodiment, CSC HP-3 homes to, targets to, or specifically binds to CSCs of a colon cancer. In another embodiment, CSC HP-3 homes to, targets to, or specifically binds to CSCs of a liver cancer.

According to one embodiment of the present invention, the synthetic peptide consists of the amino acid sequence FPFTKNL (SEQ ID NO: 4) (also called as CSC HP-4). In one embodiment, CSC HP-4 homes to, targets to, or specifically binds to CSCs of a breast cancer.

According to one embodiment of the present invention, the synthetic peptide consists of the amino acid sequence ATYGNLW (SEQ ID NO: 5) (also called as CSC HP-5). In one embodiment, CSC HP-5 homes to, targets to, or specifically binds to CSCs of a breast cancer. In another embodiment, CSC HP-5 homes to, targets to, or specifically binds to CSCs of a colon cancer.

According to one embodiment of the present invention, the synthetic peptide consists of the amino acid sequence YHMPALM (SEQ ID NO: 6) (also called as CSC HP-6). In one embodiment, CSC HP-6 homes to, targets to, or specifically binds to CSCs of a breast cancer. In another embodiment, CSC HP-6 homes to, targets to, or specifically binds to CSCs of a colon cancer.

According to one embodiment of the present invention, the synthetic peptide consists of the amino acid sequence HGGVRLY (SEQ ID NO: 7) (also called as CSC HP-7). In one embodiment, CSC HP-7 homes to, targets to, or specifically binds to CSCs of a breast cancer. In another embodiment, CSC HP-7 homes to, targets to, or specifically binds to CSCs of a colon cancer.

According to one embodiment of the present invention, the synthetic peptide consists of the amino acid sequence ELTPLTL (SEQ ID NO: 8) (also called as CSC HP-8). In one embodiment, CSC HP-8 homes to, targets to, or specifically binds to CSCs of a breast cancer. In another embodiment, CSC HP-8 homes to, targets to, or specifically binds to CSCs of a colon cancer.

According to one embodiment of the present invention, the synthetic peptide consists of the amino acid sequence GPSASRN (SEQ ID NO: 9) (also called as CSC HP-10). In one embodiment, CSC HP-10 homes to, targets to, or specifically binds to CSCs of a breast cancer.

According to one embodiment of the present invention, the synthetic peptide consists of the amino acid sequence GLAPFNA (SEQ ID NO: 10) (also called as CSC HP-11). In one embodiment, CSC HP-11 homes to, targets to, or specifically binds to CSCs of a breast cancer.

According to one embodiment of the present invention, the synthetic peptide consists of the amino acid sequence KIYTTLD (SEQ ID NO: 11) (also called as CSC HP-9).

According to one embodiment of the present invention, the synthetic peptide consists of the amino acid sequence NLQPPAY (SEQ ID NO: 12) (also called as CSC HP-12).

According to one embodiment of the present invention, the synthetic peptide consists of the amino acid sequence GPKVTIW (SEQ ID NO: 13) (also called as CSC HP-Hp1). In one embodiment, CSC HP-Hp1 homes to, targets to, or specifically binds to CSCs of a pancreatic cancer.

According to one embodiment of the present invention, the synthetic peptide consists of the amino acid sequence GSPVMSW (SEQ ID NO: 14) (also called as CSC HP-Hp2). In one embodiment, CSC HP-Hp2 homes to, targets to, or specifically binds to CSCs of a pancreatic cancer.

According to one embodiment of the present invention, the synthetic peptide consists of the amino acid sequence YHQVKPH (SEQ ID NO: 15) (also called as CSC HP-Hp3). In one embodiment, CSC HP-Hp3 homes to, targets to, or specifically binds to CSCs of a pancreatic cancer.

The synthetic peptide of the invention may be prepared or synthesized using conventional methods, for example, chemical synthesis.

According to certain embodiments of the present invention, the synthetic peptide is for use in diagnosing a cancer. According to some other embodiments of the present invention, the synthetic peptide is for use in targeting a therapeutic agent to a cancer stem cell.

According to the present invention, the synthetic peptide may be fused to a detectable moiety. In certain embodiments of the present invention, the detectable moiety is a radiolabel, a fluorophore, or a magnetic imaging contrast agent.

According to the present invention, the synthetic peptide may be fused to a therapeutic agent. In certain preferred embodiments of the present invention, the therapeutic agent is an anti-tumor agent. The anti-tumor agent includes but is not limited to a chemotherapeutic agent, a radiotherapeutic agent or an immunotherapeutic agent. The term "immunotherapeutic agent" as used herein refers to an agent which therapeutically enhances or suppresses the immune system of a subject treated by the agent.

The above described detectable moieties or therapeutic agents may be directly or indirectly bound or fused to a synthetic peptide of the present invention, for example, via a covalent bond or bound through an ionic bond.

In another aspect, the present invention provides a composition comprising a synthetic peptide according to the present invention, and a pharmaceutically acceptable carrier or diluent. Preferably, the synthetic peptide is fused to a therapeutic agent. The composition may be used as a pharmaceutical composition. The composition may be prepared by mixing the synthetic peptide with a pharmaceutically acceptable carrier or diluent, or chemically conjugating the peptide with a pharmaceutically acceptable carrier or diluent.

The synthetic peptide or composition of the present invention may be administered to a subject in need thereof by intravenous administration.

In one further aspect, the present invention provides a method of screening a peptide specifically targeting to a cancer stem cell, comprising establishing an oligopeptide library by using a phage expression system, contacting phages in the library with a culture of bulk (normal) tumor cells of a cancer cell line, contacting the phages which do not bind to the bulk tumor cells with a culture of cancer stem cells or cancer stem cell like cells of said cancer cell line, and screening a peptide specifically targeting to a cancer stem cell from the phages which bind to the cancer stem cells.

According to preferred embodiments of the present invention, the cancer stem cells or cancer stem cell like cells are derived from a tumorosphere (Weiswald et al., *Neoplasia*, 17(1): 1-15 (2015)) prepared from normal tumor cells. The tumorosphere may be prepared by a serum-free culture method. For example, a method disclosed in Eramo et al., Cell Death Differentiation, 15: 504-514 (2008); Cioce et al., Cell Cycle, 9: 2878-2887 (2010); Cao et al., BMC Gastroenterol., 11: 71 (2011); or Chen et al., Clin. Exp. Metastasis, 28(8): 751-763 (2011)).

In the prior art, peptides or other entities targeting to (normal) cancer cells have got most of the attention partially due to the small amount of cancer stem cells that can be obtained by cell culture. Further, to the inventors' knowledge, no one has proposed a strategy of screening a peptide that does not bind to normal cancer cells while binds to cancer stem cells or cancer stem cell like cells. However, the inventors unexpectedly found that through the above-mentioned method and by using cancer stem cells or cancer stem cell like cells derived from a tumorosphere, peptides that specifically bind to cancer stem cells can be effectively screened.

The present invention is further illustrated by the following examples, which are provided for the purpose of demonstration rather than limitation.

EXAMPLES

Materials and Methods

1. Cancer Cell and Cancer Stem Cell (CSC) Cultures

Although CSCs could be enriched by surface markers, such as CD44 and CD133, a practical and simple method that could selectively proliferate CSCs was critical for researches. A pioneering serum-free culture method that could selectively proliferate human lung CSCs in the suspension state was developed in 2008 (Eramo et al., Cell Death Differentiation, 15: 504-514 (2008)). Since then, CSCs of breast (Cioce et al., Cell Cycle, 9: 2878-2887 (2010)), liver (Cao et al., BMC Gastroenterol., 11: 71 (2011)), and colon (Chen et al., Clin. Exp. Metastasis, 28(8): 751-763 (2011)) were reported. The CSCs grew in a sphere-like aggregated shape that suggested nomenclature as a tumorosphere (Weiswald et al., Neoplasia, 17(1): 1-15 (2015)).

Recombinant growth factors were purchased from PeproTech. Mouse breast cancer EMT6, liver cancer Hepal-6 and human pancreatic ductal adenoma PANC-1 cell lines were maintained in DMEM supplemented with 10% FCS. The mouse colon cancer CT26 cell line was cultured in RPMI1640 supplemented with 10% FCS. The basic culture medium for CSCs was DMEM/F12 with 2 mM glutamine and the supplements for EMT6 CSCs were 25 ng/mL rmEGF, 25 ng/mL rmFGF2, 5 µg/mL insulin, 4 µg/mL heparin, 0.5 µg/mL hydrocortisone, and 1% BSA; for CT26 CSCs they were 20 ng/mL rmEGF, 5 µg/mL insulin, 2% B27, and 0.4% BSA; for Hepal-6 CSCs they were 20 ng/mL rmEGF, 10 ng/mL rmFGF2, 2% B27, and 1% N2; and for PANC-1 CSCs they were 2% B27 and 20 ng/mL rhFGF2. In order to prepare tumorospheres, cancer cells were cultured in the serum-free media at low density, e.g. <$10^4$ cells/mL. After 7 days of incubation, the tumorospheres were harvested using a 40 µm cell strainer, and they were centrifuged for 5 minutes at 900×g at room temperature. The pellets of the tumorospheres were dissociated to single cells by trypsin, and then the obtained cells were expanded into tumorospheres again for another 7 days. Growth factors were replenished every second day, and tumorospheres isolated in the third to fifth round of expansion were used for experiments.

2. M13 Phage Display

The M13 PhD-7 library (NEB, E8100) which contains $10^9$ independent clones was purchased from New England Biolabs Inc. $10^{13}$ plaque firming units (pfus) of M13 PhD-7 phages in 10 mL DMEM were pre-adsorbed by cancer cells in a T75 flask twice, each for 1 hour. Subsequently, the supernatant was transferred to a T25 flask containing 5×$10^6$ CSCs and incubated for 1 hour. The unbound and weakly associated phages were removed by centrifugation and suspension three times in DMEM/0/2% BSA. The cell pellet was suspended in 1 mL PBS containing $10^9$ *E. coli* ER2738 and incubated in a shaker for 1 hour. Then 10 mL LB/5 mM $MgCl_2$ was added. After being cultured over-night at 3TC, the cells were removed by centrifugation and phages in the supernatant were titrated. The aforementioned selection procedures were carried out for three rounds for EMT6 and PANC-1 to obtain the primary EMT6 CSC homing peptide (HP)- and PANC-1 CSC HP-library, respectively. Subsequently, M13 plaques were picked up to prepare the DNA for sequencing. The EMT6 CSC HP-library was further selected by CT26 CSCs, Hepal-6 CSCs, and mouse embryonic stem cell (mESC) again to prepare the secondary CT26 CSC HP-, Hepal-6 CSC HP-, and CSC/ES HP-library. The unbound fraction after mESC adsorption was collected and assigned as the CSC PH-library. See FIGS. 4A and 4B.

3. Binding of CSC HPs to CSCs

20 µg/mL of Rhodamine B labeled CSC HP1 (Rd-CSC HP-1) and CSC HP2 (Rd-CSC HP-2) as well as FITC labeled CSC HP11 (FITC-CSC HP-11) were directly used to stain EMT6 CSCs and CCs. Cells were counter-stained with DAPI.

4. Glycan Microarray Analysis

N-terminus biotin conjugated CSC HPs with the sequences listed in Table A below were synthesized by GeneDirex with purities higher than 95%. Biotin-CSC HPs were dissolved in DMSO to prepare 10 mg/mL stocks.

TABLE A

Biotin labeled CSC HPs

| Name | Sequence |
|---|---|
| Biotin labeled CSC HP-1 | Biotin-GGSQPTWMF (Biotin-GG-SEQ ID NO: 1) |
| Biotin labeled CSC HP-2 | Biotin-GGMMSSPP (Biotin-G-SEQ ID NO: 2) |
| Biotin labeled CSC HP-3 | Biotin-GGFSGGGNH (Biotin-GG-SEQ ID NO: 3) |
| Biotin labeled CSC HP-4 | Biotin-GGFPFTKNL (Biotin-GG-SEQ ID NO: 4) |
| Biotin labeled CSC HP-5 | Biotin-GGATYGNLW (Biotin-GG-SEQ ID NO: 5) |
| Biotin labeled CSC HP-6 | Biotin-GGYHMPALM (Biotin-GG-SEQ ID NO: 6) |
| Biotin labeled CSC HP-7 | Biotin-GGHGGVRLY (Biotin-GG-SEQ ID NO: 7) |
| Biotin labeled CSC HP-8 | Biotin-GGELTPLTL (Biotin-GG-SEQ ID NO: 8) |
| Biotin labeled CSC HP-9 | Biotin-GGKIYTTLD (Biotin-GG-SEQ ID NO: 11) |
| Biotin labeled CSC HP-10 | Biotin-GGPSASRN (Biotin-G-SEQ ID NO: 9) |
| Biotin labeled CSC HP-11 | Biotin-GGLAPFNA (Biotin-G-SEQ ID NO: 10) |
| Biotin labeled CSC HP-12 | Biotin-GGNLQPPAY (Biotin-GG-SEQ ID NO: 12) |
| Biotin labeled CSC HP-hP1 | Biotin-GGPKVTIW (Biotin-G-SEQ ID NO: 13) |
| Biotin labeled CSC HP-hP2 | Biotin-GGSPVMSW (Biotin-G-SEQ ID NO: 14) |
| Biotin labeled CSC HP-hP3 | Biotin-GGYHQVKPH (Biotin-GG-SEQ ID NO: 5) |

Glycan Array 100 microchips (Cat. # GA-Glycan-100) were purchased from RayBiotech and were processed following the manufacturer's instruction with some modifications. Briefly, after blocking with 400 µL Sample Diluent (Item E) at room temperature for 30 minutes, the biotin conjugated CSC HPs were diluted to 1 µg/400 µL with Sample Diluent, and hybridization reactions were carried out at room temperature for 2 hours. After washing, 400 µL of 1×Cy3-conjugated streptavidin was added to each well. The incubation chamber was covered with the plastic adhesive strips and the slide was covered with aluminum foil to avoid exposure to light during incubating in a dark room. The slide was incubated with Cy3-conjugated streptavidin at room temperature for 1 hour with gentle rocking or shaking. After thorough washing, the slide was drained completely, and the fluorescent signals on it were read by laser scanner Axon GenePix. The relative intensity on glycan X was defined as (average of X−negative control)/(positive control−negative control)×100%.

5. Immunofluorescence (IF) Assay

The primary antibodies rabbit polyclonal anti-CD44 (GTX102111), anti-E-cadherin (GTX61823) and anti-CDSN (GTX110093) as well as mouse monoclonal anti SSEA-1 (IgM, GTX48038), anti SSEA-5 (IgG, GTX70019), and anti-Lewis Y (IgM, GTX75903) were purchased from GeneTex; mouse monoclonal anti-SSEA-4 (IgG, 90230), anti-TRA-1-60 and TRA-1-81 (IgM, in 90232) were from Millipore; mouse monoclonal anti-GbH (IgM, ALX-804-550) was from Enzo. The secondary antibodies DyLight594-conjugated goat anti-rabbit IgG (111-515-144) and DyLight488-conjugated donkey anti-mouse IgG (715-485-151) were obtained from Jackson Lab.; DyLight594-conjugated goat anti-mouse IgM (GTX76754) was obtained from GeneTex. Cancer cells and tumorospheres were fixed by 4% paraformaldehyde/PBS and permeabilized by 0.5% NP-40/ 1% BSA/PBS (PBSNB). Then the cells were incubated with primary antibodies that were diluted in PBSNB by 50 to 100 fold for two hours. After 4 times washes with 0.05% NP-40/PBS (PBSN), the cells were incubated with secondary antibodies (1/200 dilution in PBSNB) for 2 hours. After 4 washes with PBSN and one brief wash with water, the cells were mounted with DAPI.

Example 1: Identifications of Mouse EMT6, CT26 and Hepal-6 CSCs

The criteria to select peptides displayed by M13 phage specific to cancer stem cells were dependent on the differences of the surface features between CSCs and the cancer cells (CCs). The mouse EMT6, CT26 and Hepal-6 CSCs prepared in the tumorosphere forms (data not shown) were identified by checking the specific stem cell surface markers. The stem cell surface marker TRA-1-60 was highly expressed on all three CSCs, but its expression was low or undetectable on the corresponding CCs, while the constitutively expressed surface protein corneodesmosin (CDSN) was detected on both CSCs and CCs (data not shown). Except for SSEA-4, which was illustrated as weakly expressed on EMT6 CSCs, all of the human CSC general marker, CD44 and E-cadherin, as well as the pluripotent stem cell markers, SSEA-1, SSEA-5, TRA-1-60 and TRA-1-81, were demonstrated as strongly expressed on all three mouse CSCs (data not shown).

Example 2: Primary EMT6 CSC HP-Library

In order to explore CSC specific HPs, the M13 PhD7 hepta-peptide library was pre-adsorbed by EMT6 CCs to remove the general cancer HPs, then the free phages were transferred to EMT6 CSCs for positive selection. The phages associated on EMT6 CSCs were trapped and amplified by E. coli ER2738. The aforementioned selection procedures were carried out for three rounds to prepare an enriched primary EMT6 CSC HP library. Independent plaques were randomly picked and 31 valid sequences were read and summarized in Table 1 below.

TABLE 1

The times of CSC HP sequences detected in the primary and secondary CSC HP-libraries

| CSC HPs | | Primary | | | Secondary | |
|---|---|---|---|---|---|---|
| Name | Sequence | EMT6 (n = 31) | CT26 (n = 20) | Hepa1-6 (n = 10) | CSC/ESC (n = 20) | CSC (n = 20) |
| CSC HP-1 | SQPTWMF | 10 | 6 | | 11 | 8 |
| CSC HP-2 | GMMSSPP | 6 | 3 | | 1 | 1 |
| CSC HP-3 | FSGGGNH | 5 | 1 | 10 | 1 | 1 |
| CSC HP-4 | FPFTKNL | 3 | | | 2 | 2 |
| CSC HP-5 | ATYGNLW | 2 | 1 | | 1 | 2 |
| CSC HP-6 | YHMPALM | 1 | 1 | | 1 | 2 |
| CSC HP-7 | HGGVRLY | 1 | 1 | | 1 | 2 |
| CSC HP-8 | ELTPLTL | 1 | 7 | | 2 | |
| CSC HP-9 | KIYTTLD | | | | | 1 |
| CSC HP-10 | GPSASRN | 1 | | | | |
| CSC HP-11 | GLAPFNA | 1 | | | | |
| CSC HP-12 | NLQPPAY | | | | | 1 |

Peptides SQPTWMF (called as CSC HP-1) (SEQ ID NO: 1), GMMSSPP (called as CSC HP-2) (SEQ ID NO: 2), FSGGGNH (called as CSC HP-3) (SEQ ID NO: 3), FPFTKNL (called as CSC HP-4) (SEQ ID NO: 4), and ATYGNLW (called as CSC HP-5) (SEQ ID NO: 5) occurred 10, 6, 5, 3, and 2 times, respectively. Peptides YHMPALM (called as CSC HP-6) (SEQ ID NO: 6), HGGVRLY (called as CSC HP-7) (SEQ ID NO: 7), ELTPLTL (called as CSC HP-8) (SEQ ID NO: 8), GPSASRN (called as CSC HP-10) (SEQ ID NO: 9), and GLAPFNA (called as CSC HP-11) (SEQ ID NO: 10) appeared once. Since the M13 PhD7 library was estimated to contain $10^9$ independent clones, it can be concluded that the selection procedures were highly effective.

Example 3: Secondary CT26 CSC HP-, Hepa1-6 CSC HP-, CSC/ESC HP- and CSC HP-Libraries The primary CSC HP-library was selected directly once by either CT26 or Hepa1-6 CSCs to test the bias of CSC HP affinities to different kinds of cancers. As shown in Table 1, CSC HP-8 and CSC HP-3 were more specific to CT26 and Hepa1-6 CSCs, respectively. The bias of CSC HP affinities between CSCs and embryonic stem cells (ESCs) was another interesting issue. The CSC HP-1 was further enriched in the ESC bound fraction (CSC/ESC-HP-library). Two new peptide sequences, KIYTTLD (CSC HP-9) (SEQ ID NO: 11) and NLQPPAY (CSC HP-12) (SEQ ID NO: 12), were read in the ESC unbound fraction (CSC HP-library) (Table 1).

Example 4: Interactions Between CSC HPs and CSCs

According to the results above, CSC HP-1, CSC HP-2, CSC HP-3, CSC HP-8, CSC HP-9, CSC HP-10, and CSC HP-11 were selected and chemically synthesized with N-terminal conjugation with rhodamine B or fluorescein. All of these peptides specifically associated with EMT6, CT26 and Hepal-6 CSCs. They were not detectable in the parallel CC experiments (FIG. 1A and FIG. 1B). It was of interest to determine whether these CSC HPs derived from mouse cancers could recognize human CSCs. Tumorospheres prepared from the human pancreatic cancer cell line PANC-1 were found to be definitely associated with the seven peptides (FIG. 1B).

Example 5: Primary PANC-1 CSC HP Library

If the CSC HPs selected by mouse CSCs could cross-react with human CSCs, could the CSC HPs selected by human CSCs associate with mouse CSCs? Following the similar procedures for EMT6 CSC HP screening, after three rounds of negative selection with human pancreatic PANC-1 CCs and positive selection with PANC-1 CSCs, a primary PANC-1 CSC HP-library was established. Independent plaques were randomly picked and 20 valid sequences were read. Peptide GPKVTIW (as signed as CSC HP-hP1), GSPVMSW (CSC HP-hP2), and YHQVKPH (CSC HP-hP3) occurred 17, 2, and 1 times, respectively. See Table 2 below.

TABLE 2

The times of CSC HP sequences detected in the primary PANC-1CSC HP-libraries

| CSC HP | | Primary PANC-1 |
|---|---|---|
| Name | Sequence | (n = 20) |
| CSCHP-hP1 | GPKVTIW (SEQ ID NO: 13) | 17 |
| CSCHP-hP2 | GSPVMSW (SEQ ID NO: 14) | 2 |
| CSCHP-hP3 | YHQVKPH (SEQ ID NO: 15) | 1 |

The amino acid sequences of the CSC HP-hP series did not match those of the mouse CSC HPs. In addition to chemically synthesized FITC-CSC HP-hP1, which could selectively associate with both human and mouse CSCs (data not shown), CSC HP-hP1-DsRed recombinant protein was prepared to test whether the interactions between CSC HP-hP1 and PANC-1 CSCs would be affected by a large molecule cargo fused to the C-terminus of CSC HP-hP1 peptide. The CSC HP-hP1-DsRed recombinant protein was demonstrated to be selectively bound to PANC-1 CSCs, while a few cells within the CCs were also stained by the recombinant protein as the arrow heads in FIG. 2 indicated.

Example 6: Targets of the CSC HPs

The CSC HPs developed could distinguish CSCs from CCs, and this phenomenon was found cross-species between human and mouse. It was very interesting to figure out the targets of these CSC HPs. There were no detectable fluorescent signals of FITC-CSC HPs remaining on the nitrocellulose membrane that had been blotted with CSC membrane proteins separated by SDS PAGE (data not shown). Glycan microarray (Glycan Array 100 microchips), on which 100 kinds of oligosaccharides were spotted 4 times, was utilized to analyze the possibilities of the interactions between oligosaccharides and CSC HPs. Biotin-CSC HPs as listed in Table 2 were hybridized with glycans on chips. The biotin-CSC HPs trapped on the chips were explored with Cy3-conjugated streptavidin, and the fluorescent signals on it were read by a laser scanner. Two major patterns were illustrated in FIGS. 3A-3F. The first one included glycan 16 (Gal-β-1,4-Glc-β-), 18 (Gal-α-1,4-Gal-β-1,4-Glc-β-), and 26 (GalNAc-β-1,3-Gal-α-1,4-Gal-β-1,4-Glc-β-) Globo series (FIG. 3A). Typical cases were CSC HP-1 and CHC HP-hP1 (FIG. 3C). In addition to the Globo series signals, the second major pattern involved the glycan 19 (GlcNAc-β-1,3-Gal-β-1,4-Glc-β-, which is Lacto/Isolacto tri-saccharide backbone), which was similar to the level of glycan 26 (FIG. 3B). The typical cases were CSC HP5, CSC HP6, CSC HP7, and CSC HP9 (FIG. 3C). Two malignancy and metastasis glycan markers, glycan 63 (Fuc-α-1,2-Gal-β-1,4-(Fuc-α-1,3)-GlcNAc-β-, also called Lewis Y epitope) and glycan 69 (Neu5Ac-α-2,6-Gal-β-1,3-(Neu5Ac-α-2,6)-GalNAc-β-), were also detected. CSC HP-1 and CSC HP-hP1 performed higher signals on glycan 63, and CSC HP-9, CSC HP-10, CSC HP-11, CSC HP-hP2, and CSC HP-hP3 performed higher signals on glycan 69 (FIG. 3D). Both of the two Neu5Ac-α-2,6- residues were necessary for CSC HPs binding (FIG. 3E). According to the aforementioned results, CSCs of human pancreatic cancer cell PANC-1 were prepared, and the CSC glycan markers of the Globo series, SSEA-4 and GbH, Lacto/Isolacto series, SSEA-1 and SSEA-5, as well as Lewis Y, were all demonstrated on PANC-1 CSCs by IF assays as shown in FIG. 3F.

According to the glycan microarray data, CSC HP-1 and CSC HP-hP1 bound strongly and specifically to glycan 26, which is the Globo root structure of tetrasaccharides. On the other hand, CSC HP5, CSC HP6, CSC HP7, and CSC HP9 bound strongly to glycan 19, which is the core trisaccharide of Lacto and Neolacto root structure tetrasaccharides. The CSC HP-3 and CSC HP-8, thought to be specific to liver and colon CSCs, respectively, were found weakly bound to glycan 26. CSC HP-1 and CSC HP-hP1 were the two CSC HP members that bound more strongly to glycan 63, Lewis Y epitope.

What is claimed is:

1. A synthetic peptide that targets cancer stem cells, which is selected from the group consisting of the amino acid sequences of SEQ ID NOS: 1-15, the synthetic peptide being fused to a detectable moiety or a therapeutic agent.

2. The synthetic peptide of claim 1 for use in diagnosing a cancer.

3. The synthetic peptide of claim 1 for use in targeting a therapeutic agent to a cancer stem cell.

4. The synthetic peptide of claim 1, wherein the detectable moiety is a radiolabel, a fluorophore or a magnetic imaging contrast agent.

5. The synthetic peptide of claim 1, wherein the therapeutic agent is an anti-tumor agent.

6. The synthetic peptide of claim 5, wherein the anti-tumor agent is a chemotherapeutic agent, a radiotherapeutic agent or an immunotherapeutic agent.

7. A composition comprising the synthetic peptide according to claim 1 and a pharmaceutically acceptable carrier or diluent.

* * * * *

SEQUENCE LISTING

```
<160> NUMBER OF SEQ ID NOS: 15

<210> SEQ ID NO 1
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 1

Ser Gln Pro Thr Trp Met Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 2

Gly Met Met Ser Ser Pro Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 3

Phe Ser Gly Gly Gly Asn His
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 4

Phe Pro Phe Thr Lys Asn Leu
1               5

<210> SEQ ID NO 5
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 5

Ala Thr Tyr Gly Asn Leu Trp
1               5

<210> SEQ ID NO 6
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 6

Tyr His Met Pro Ala Leu Met
1               5

<210> SEQ ID NO 7
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 7

His Gly Gly Val Arg Leu Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 8

Glu Leu Thr Pro Leu Thr Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 9

Gly Pro Ser Ala Ser Arg Asn
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 10

Gly Leu Ala Pro Phe Asn Ala
1               5

<210> SEQ ID NO 11
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 11

Lys Ile Tyr Thr Thr Leu Asp
1               5

<210> SEQ ID NO 12
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 12

Asn Leu Gln Pro Pro Ala Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 13

Gly Pro Lys Val Thr Ile Trp
1               5

<210> SEQ ID NO 14
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 14

Gly Ser Pro Val Met Ser Trp
1               5

<210> SEQ ID NO 15
<211> LENGTH: 7
<212> TYPE: PRT
<213> ORGANISM: Artificial Sequence
<220> FEATURE:
<223> OTHER INFORMATION: Cancer Stem Cell Targeting Peptide

<400> SEQUENCE: 15

Tyr His Gln Val Lys Pro His
1               5
```